United States Patent [19]

Mushika et al.

[11] Patent Number: 4,942,735
[45] Date of Patent: Jul. 24, 1990

[54] APPARATUS FOR DRIVING A MEDICAL APPLIANCE

[75] Inventors: Sadahiko Mushika, Ichinomiya; Akira Suzuki, Nishio, both of Japan

[73] Assignees: Aisin Seiki Kabushiki Kaisha, Aichi; Kabushiki Kaisha Shinsangyokaihatsu, Tokyo, both of Japan

[21] Appl. No.: 246,232

[22] Filed: Sep. 19, 1988

[30] Foreign Application Priority Data

Sep. 18, 1987 [JP] Japan ................................. 62-23582

[51] Int. Cl.⁵ ............................................. F16D 31/02
[52] U.S. Cl. ........................................ 60/416; 60/418; 91/265; 91/275; 417/395; 600/16
[58] Field of Search ................... 417/394, 395; 60/415, 60/416, 418, 468; 600/16; 91/265, 271, 275, 459

[56] References Cited

U.S. PATENT DOCUMENTS

| 3,163,985 | 1/1965 | Bouyoucos | 60/416 |
| 3,490,337 | 1/1970 | Klein | 91/459 |
| 4,548,550 | 10/1985 | Tsuji | 417/394 |
| 4,731,997 | 3/1988 | Hagin | 60/416 |
| 4,754,603 | 7/1988 | Rosman | 60/468 |

FOREIGN PATENT DOCUMENTS 1326391  4/1963  France .

Primary Examiner—Edward K. Look
Assistant Examiner—John E. Ryznic
Attorney, Agent, or Firm—Sughrue, Mion, Zinn, Macpeak & Seas

[57] ABSTRACT

Apparatus for driving a medical appliance has a single compressor for generating both the positive and negative pressures. The switching valves are connected to the outlet and inlet terminals of the compressor. The outlet and inlet terminals of the compressor are also connected to the positive pressure accumulator and the negative pressure accumulator, respectively. The apparatus has the pressure sensors to sense the pressures in the positive and negative pressure accumulators. When the pressure in the accumulator reaches a set pressure, at least one of the switching valves is closed. The apparatus further has the relief valves connected to the outlet and inlet terminals of the compressor. These relief valves open when the pressures of the compressor become excessive.

3 Claims, 5 Drawing Sheets

APPARATUS FOR DRIVING A MEDICAL APPLIANCE

BACKGROUND OF THE INVENTION

The present invention relates to an apparatus for driving a medical appliance such as an artificial heart or balloon pump in the artery, and more particularly to a fluid driving apparatus for changing a positive fluid pressure and a negative fluid pressure.

The conventional driving apparatus for a medical appliance is shown in, for example, Japanese Patent Laid-Open Application No. 61(1986)-12900. In this conventional apparatus, the apparatus has one compressor for producing both positive and negative pressures. An outlet terminal of the compressor is connected to a one-way valve and a switching valve and an inlet terminal of the compressor is also connected to a one-way valve and a switching valve. When it is in a positive pressure applying period, positive pressure regulation has priority. On the other hand, when it is in a negative pressure applying period, negative pressure regulation has priority. If both a positive and a negative pressure are above each setting pressure, respectively, both switching valves are opened. Thus the compressor is idle, because the compressor draws air from the atmosphere and exhausts air to the atmosphere. Then this apparatus can generate both positive and negative pressures by a single compressor.

However, this apparatus makes undesirable noise because the compressor is often operated in the idle mode. Furthermore, when the compressor operates in the idle mode, power consumption may increase.

SUMMARY OF THE INVENTION

Accordingly, one of the objects of the present invention is to produce an apparatus to obviate the above drawbacks. That is to generate both positive and negative pressures by using a single compressor and to eliminate the condition in which the compressor operates in the idle mode.

Another object of the present invention is to produce an apparatus which stores an excess of pressure and to reduce it's power consumption and it's size.

To achieve the above objects, and in accordance with the principles of the invention as embodied and broadly described herein, an apparatus for driving a medical appliance comprises a positive pressure generating means, a first one-way valve means having an inlet terminal connected to an outlet terminal of the positive pressure generating means, a first accumulating means connected to an outlet terminal of the first one-way valve means, a first switching valve means connected to the first accumulating means, a first pressure sensing means for detecting a pressure between the first one-way valve means and the first switching valve means, a second switching valve means connected to an outlet terminal of the first switching valve means, a second accumulating means connected to the second switching valve means, a second one-way valve means having an inlet terminal connected to the second accumulating means and an outlet terminal connected to an inlet terminal of the positive pressure generating means, a second pressure sensing means for detecting a pressure between the second switching valve means and the second one-way valve means, a third switching valve means connected to the inlet terminal of the first one-way valve means, a fourth switching valve means connected to the outlet terminal of the second one-way valve means, an electronic control means for opening and closing the first and second switching valve means in accordance with predetermined timings, for opening and closing the third and fourth switching valve means in accordance with both positive and negative pressure setting values provided in the electronic control means and output signals from the first and second pressure sensing means and for closing at least one of the third and fourth switching valve means if at least one of the output signals from the first and second pressure sensing means is above the setting values, respectively.

In such driving apparatus, pressures of the first and second accumulator means are controlled to positive and negative setting pressures, respectively. When at least one of the third and fourth switching valves is closed, some load is applied to the compressor and an idle operation of the compressor is prevented.

BRIEF DESCRIPTION OF THE DRAWINGS

For a full understanding of the true scope of the invention, the following detailed description should be read in conjunction with the drawings wherein.

DETAILED DESCRIPTION OF THE PREFERRED EMBODIMENTS

In the following, preferred embodiments of the present invention will be described with reference to the drawings.

Figure 1:
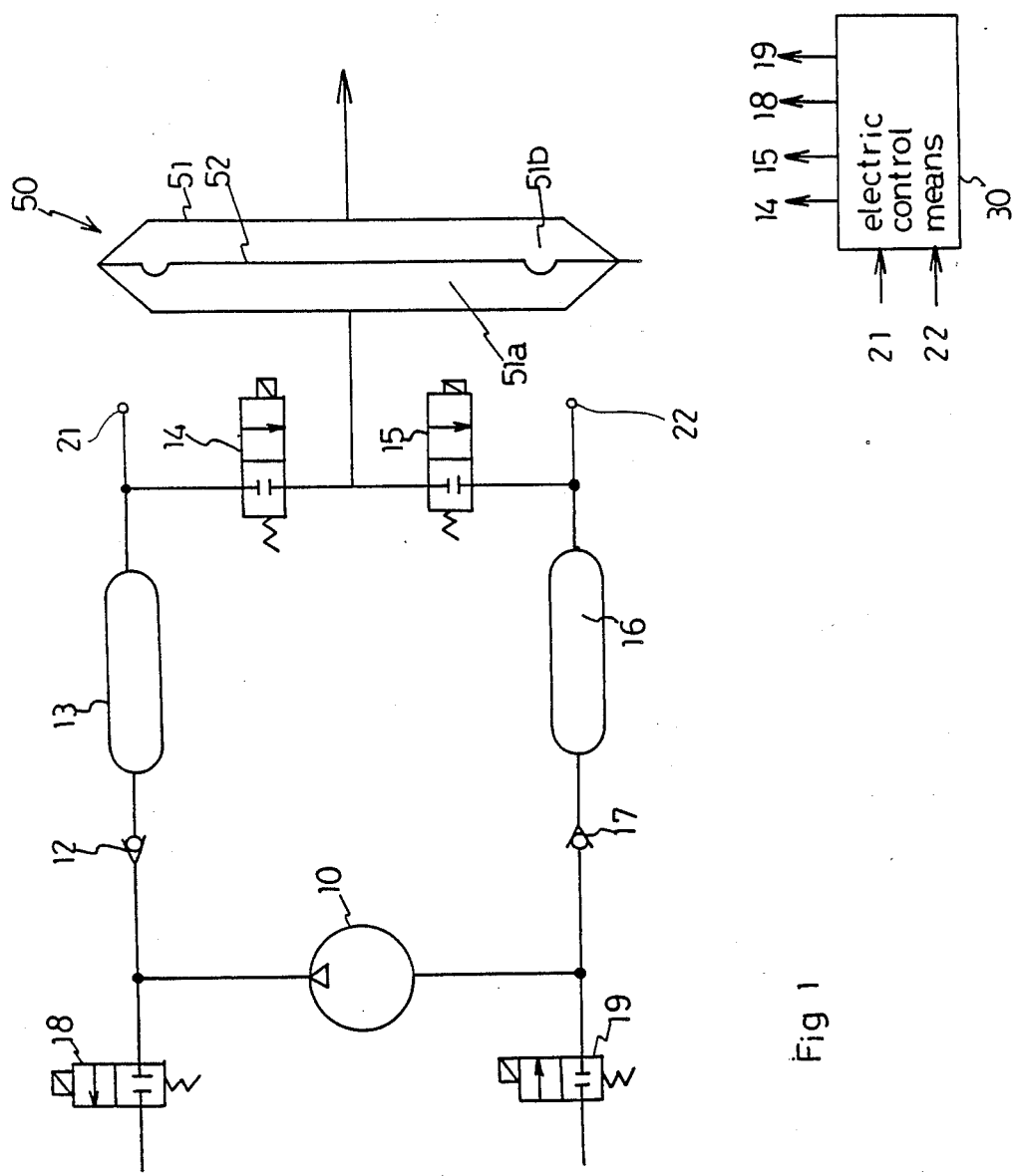
FIGS. 1 is a block diagram showing the system configuration of the apparatus of this invention.

FIG. 1 is a block diagram showing the system configuration of the apparatus of this invention. Referring to FIG. 1, an outlet terminal of a compressor 10 as a positive pressure generating means, is connected to an inlet terminal of a first one-way valve 12. An outlet terminal of the first one-way valve 12 is connected to an inlet terminal of a first accumulator 13. The first accumulator 13 is connected to a first switching valve 14, an outlet terminal of the first switching valve 14 is connected to an inlet terminal of a second switching valve 15. An outlet terminal of the second switching valve 15 is connected to a second accumulator 16 and the second accumulator 16 is connected to an inlet terminal of a second one-way valve 17. An outlet terminal of the second one-way valve 17 is connected to the inlet terminal of the compressor 10. Thus the inlet and outlet terminals of the compressor 10 makes a closed loop through the valves.

A first pressure sensing means 21 is connected between the first accumulator 13 and the first switching valve 14. A second pressure sensing means 22 is connected between the second accumulator 16 and the second switching valve 15.

Between the outlet terminal of the compressor 10 and the first one-way valve 12, an inlet terminal of a third switching valve 18 is connected. Between the inlet terminal of the compressor 10 and the second one-way valve 17, a fourth switching valve 19 is connected. The outlet terminal of the third switching valve 18 and the inlet terminal of the fourth switching valve 19 are connected to the atmosphere.

The outlet signals from the first and second pressure sensing means 21 and 22 are connected to electronic control means 30. The output signals from the electronic control means 30 are connected to the switching valves 14, 15, 18 and 19.

In the aforementioned apparatus, between the first switching valve 14 and the second switching valve 15 is provided an output. This output is connected to a medical appliance through an isolator 50. The isolator 50 prevents air from entering into a medical appliance such as an artificial heart pump or a balloon pump, when such a medical appliance is driven by fluid such as a helium gas. The isolator 50 is divided into two parts by a diaphragm 52 provided in a housing 51. An air chamber 51a is connected to the driving apparatus and a helium chamber 51b is connected to a medical appliance and helium gas supplying mechanism (not shown).

Figure 2:
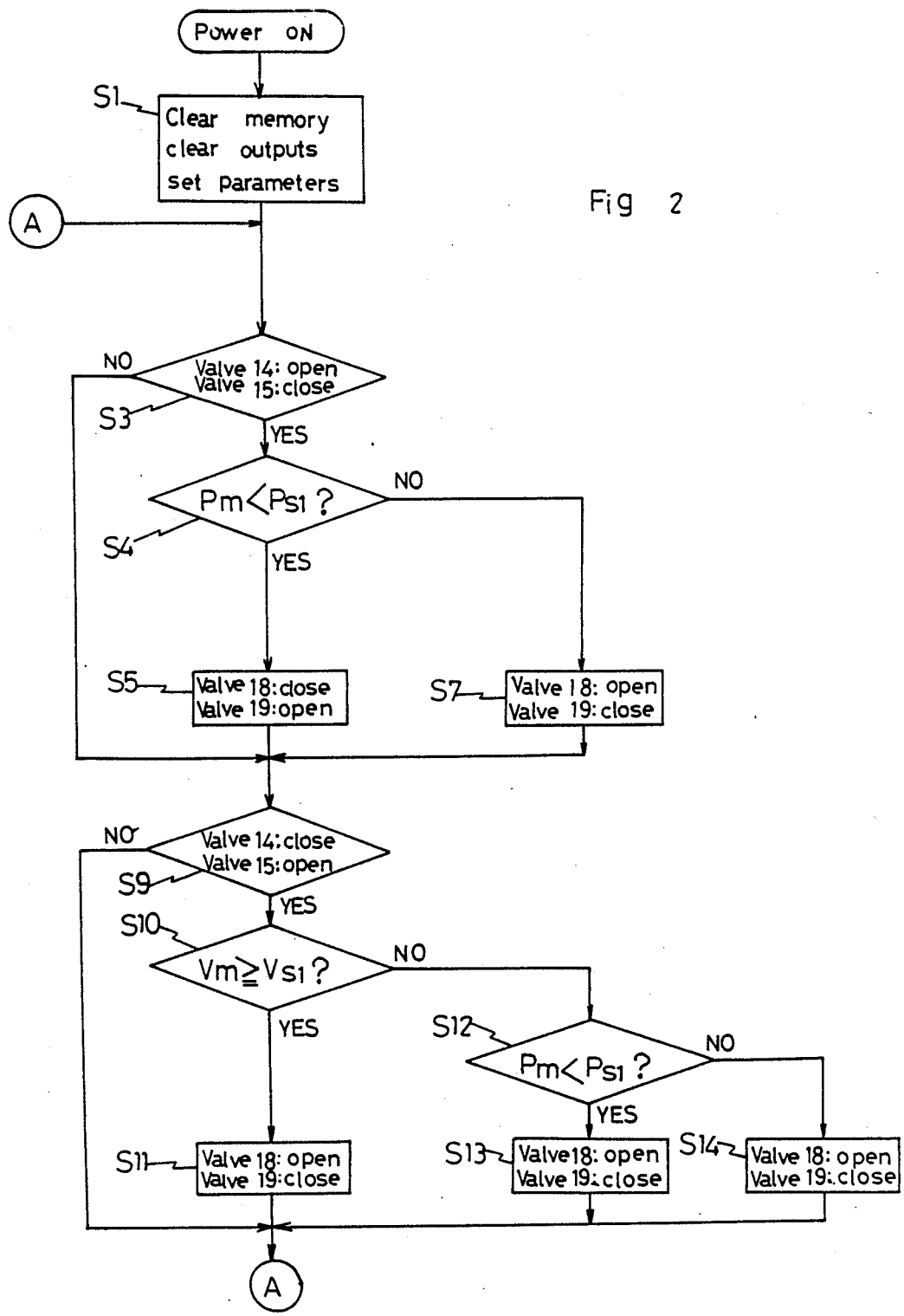
FIGS. 2 and 3 are flow charts showing the operation of the electronic control means of this invention.
Figure 3:
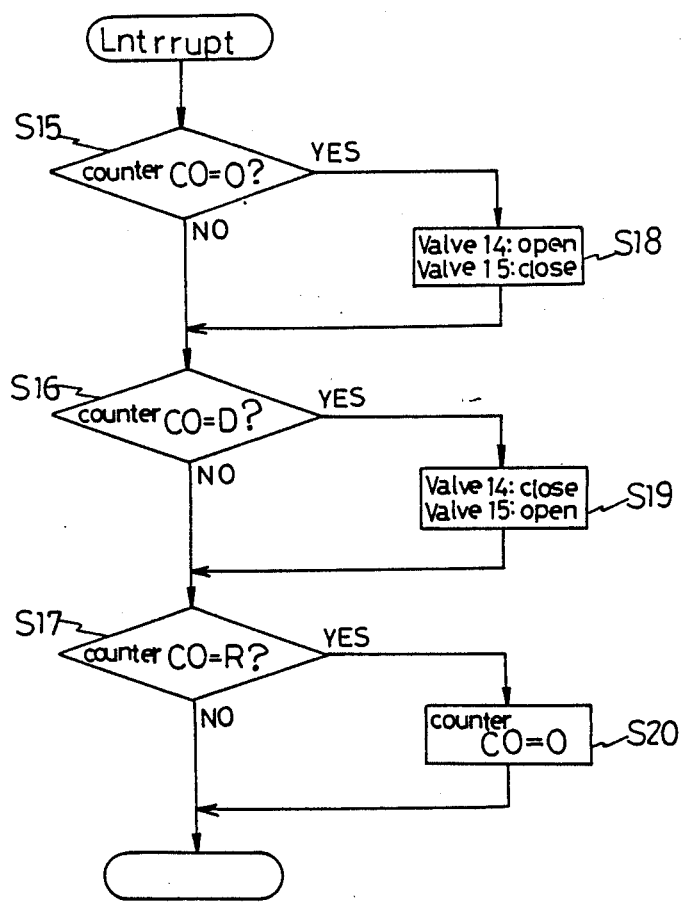

FIGS. 2 and 3 illustrate the schematic operation of the electronic control means 30. FIG. 2 shows a main routine and FIG. 3 shows an interrupt processing routine. Description will be made with reference to FIGS. 2 and 3.

When powered on the electronic control means clears the contents of memory and output signals and sets the parameters at initial values. As to these parameters, for example, heart beats and duty ratio of heart beats are provided when the apparatus is used for an artificial heart pump. After the above, an interruption is allowed. Referring to FIG. 3, a counter counts up one if the interrupt processing routine is executed. When the value of the counter shows "R", the value is cleared to "0", the first switching valve 14 is opened and the second switching valve 15 is closed (S 15 and S 18). Thus the positive pressure is supplied to the isolator 50. When the value of the counter shows "D", the first switching valve 14 is closed and the second switching valve 15 is opened. Then the negative pressure is supplied to the isolator 50. When the value of the counter shows "R", again the value of the counter is cleared to "0". As mentioned above, a timing is decided by the set values of the counter, those are "R" and "D", and by this timing positive and negative pressures are supplied to the isolator 50, alternately.

Returning to FIG. 2, the pressure regulating process will now be explained. There are two pressure modes in accordance with the conditions of the first and second switching valves 14 and 15. Therefore, pressure regulation is divided into two parts. After the interrupt processing routine, a judgment will be made whether the first switching valve is open and the second switching valve is closed or not in step S3. This judgment determines whether a positive pressure is supplied (positive pressure supplying mode) or not. If the judgment is "yes", that is, the positive pressure supplying mode, the output signal from the first pressure sensing means 21 is compared with the first positive pressure set value Ps1. If the sensed pressure Pm is less than the set value Ps1, the third switching valve 18 is closed and the fourth switching valve 19 is opened (S 5). Accordingly, the air is supplied to the inlet terminal of the compressor 10 through the fourth switching valve 19. All the positive pressure generated by the compressor 10 is supplied to the first accumulator 13 through the first one-way valve 12. Thus the positive pressure is regulated if the supplied positive pressure is less than the set value in the positive pressure supplying mode. On the contrary, when the sensed pressure Pm is above the first set value Ps1, because the positive pressure is enough in this circumstance, the third switching valve 18 is opened and the fourth switching valve 19 is closed [S 7]. Thus the positive pressure generated by the compressor 10 is released to the atmosphere through the third switching valve 18. Because the fourth switching valve is closed in this condition, the compressor 10 reduces the pressure of the second accumulator 16.

According to this control, the pressure of the second accumulator 16 can be reduced to the level in which the compressor 10 is rocked. Therefore, the second accumulator 16 accumulates the pressure lower than the negative set pressure. If the medical appliance which is connected to the isolator 50 is a balloon pump, for example, since the isolator 50 absorbs shocks when excessive pressure is applied to the isolator 50, there is little possibility of the balloon pump being destroyed. When the lower pressure is applied to the isolator 50, the balloon pump is deflated quickly and sharply. Further the accumulator can store extra negative pressure so that the balloon pump can respond when the heart beats faster or suddenly.

The condition in which the first switching valve 14 is closed and the second switching valve 15 is opened is the negative pressure supplying mode. When the judgment is made that the first switching valve 14 is closed and the second switching valve 15 is opened at the step S9, a sensed pressure Vm of the second pressure sensing means 22 is compared with the first negative set pressure Vs1.

If the sensed pressure Vm is equal or greater than the set value Vs1, the third switching valve 18 is opened and the fourth switching valve 19 is closed (S 11). Accordingly, the compressor 10 draws the air from the second accumulator 16 through the inlet terminal of the compressor 10 and exhausts the air from the outlet terminal of the compressor 10 to the atmosphere through the third switching valve 18. When the sensed pressure Vm is detected to be less than the first negative set pressure Vs1 in step S 10, the control goes to step S 12. In step S 12, the sensed pressure Pm of the first pressure sensing means 21 is compared with the first positive set pressure Ps1. When the sensed pressure Pm is less than the first positive set pressure Ps1, the third switching valve 18 is closed and the fourth switching valve 19 is opened. Then the positive pressure is supplied to the first accumulator 13. When the sensed pressure Pm is above the first positive pressure Ps1, the third switching valve 18 is opened and the fourth switching valve 19 is closed.

According to this control, when the control is under negative pressure supplying mode, the negative pressure in the second accumulator 16 is regulated. If the negative pressure in the second accumulator 16 is regulated to the set pressure, the positive pressure in the first accumulator 13 is regulated. Therefore, during the negative pressure supplying mode a positive pressure is also provided for the next positive pressure supplying mode. Further, if the positive pressure in the first accumulator 13 reaches the positive set pressure, the negative pressure in the second accumulator 16 is reduced further. Then the negative pressure is provided for the next negative supplying mode.

As mentioned above, in this embodiment the compressor 10 is driven to reduce the pressure in the second accumulator 16 when the sensed pressures reach to the set pressures in each positive and negative pressure supplying mode. At that time though, the third switching valve 18 is opened, the fourth switching valve 19 is closed. Then a load to the inlet terminal of the compressor 10 is increased, and the compressor 10 is prevented from an idle operation.

Figure 4:
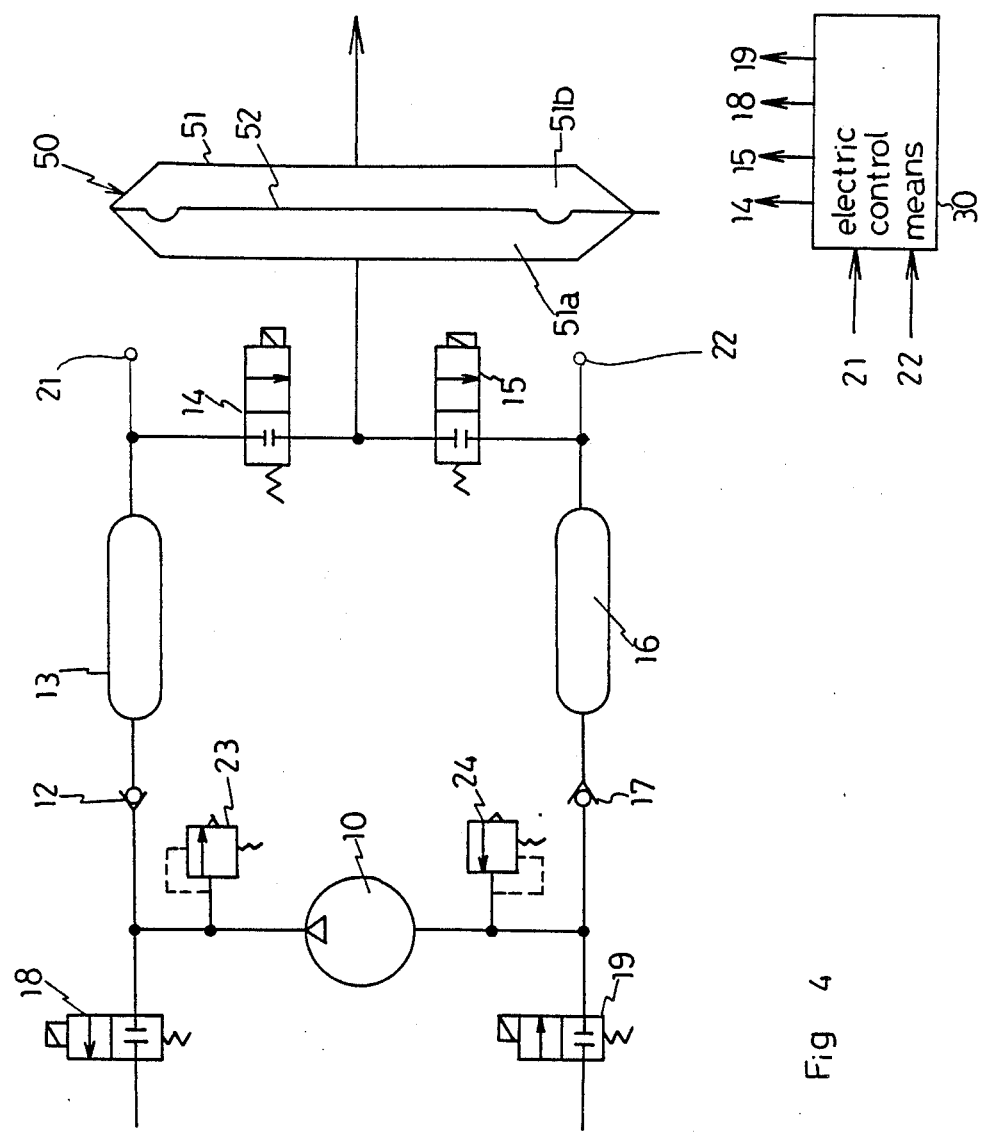
FIG. 4 is a block diagram showing the system configuration of another embodiment of this invention.

FIG. 4 shows another embodiment of this invention. This embodiment is useful if the compressor is very powerful and it may be dangerous to apply full power to generate a pressure.

Figure 5:
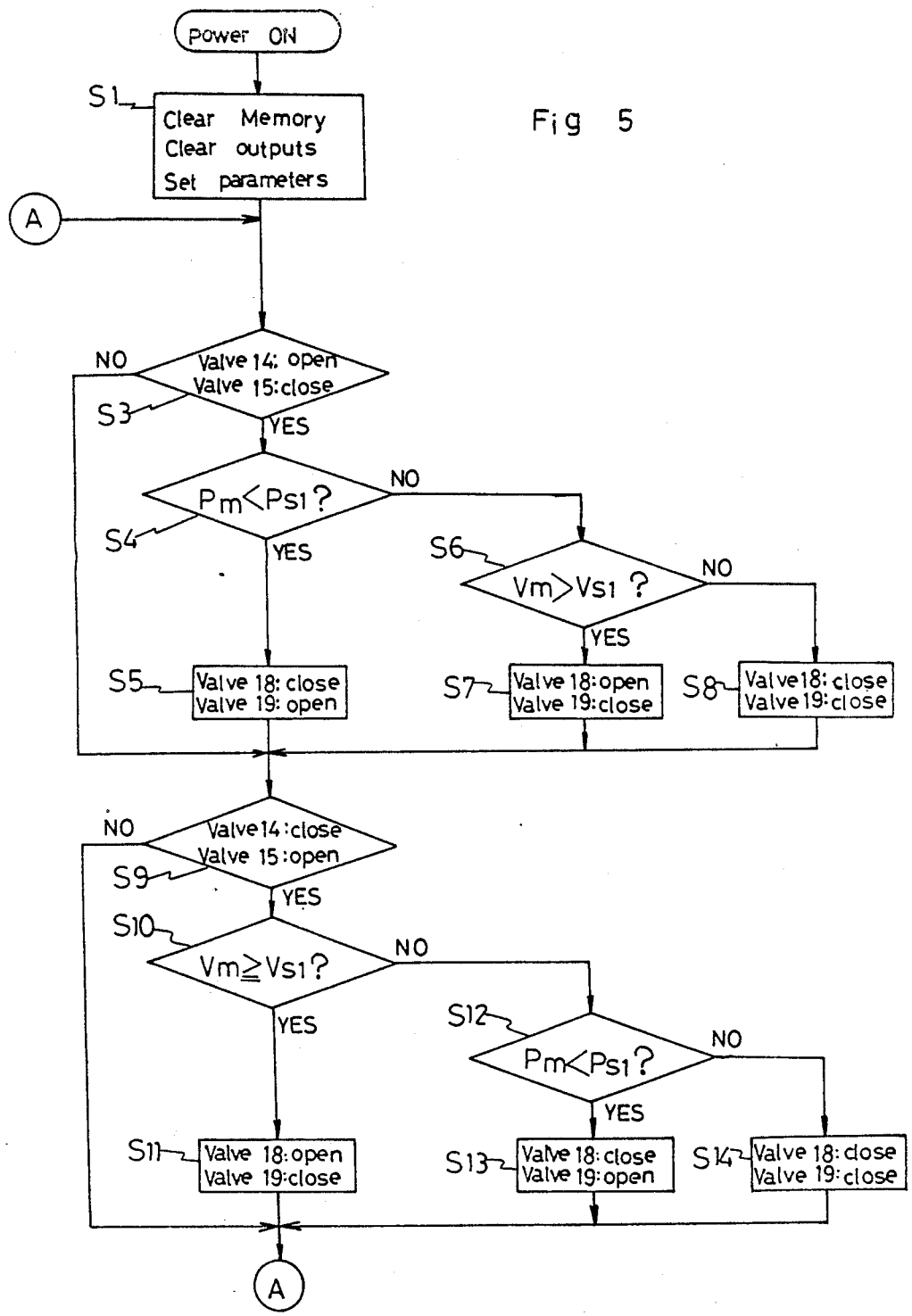
FIG. 5 is a flow chart showing the operation of the electronic control means in FIG. 4.

Referring to FIG. 4, a positive pressure relief valve 23 is connected to the outlet terminal of the compressor 10 and a negative pressure relief valve 24 is connected to the inlet terminal of the compressor 10. The positive pressure relief valve 23 is set to the second positive pressure set value Ps2 in order to communicate to the atmosphere at that set value Ps2. The negative pressure relief valve 24 is set to the second negative pressure set value Vs2 in order to communicate to the atmosphere at that set value Vs2. Other elements are the same as the elements in the first embodiment shown in FIG. 1. Referring to FIG. 5, the operation will be explained. In the positive pressure supplying mode, if the sensed pressure Pm of the first pressure sensing means 21 reaches the first positive pressure set value Ps1, the sensed pressure Vm of the second pressure sensing means 22 is compared with the first negative pressure set value Vs1 at step S 6. If the sensed pressure Vm is less than the first negative pressure set value Vs1, the third switching valve 18 is opened and the fourth switching valve 19 is closed at step S 7. Thus a negative pressure is supplied to the second accumulator 16. If the sensed pressure Vm reaches to the first negative pressure set value, the third and fourth switching valves 18 and 19 are closed at step S 8.

Under this positive pressure supplying mode, when the pressure in the first accumulator 13 reaches to the first positive pressure set value Ps1, the pressure in the second accumulator 16 is regulated to the first negative pressure set value Vs1. When the negative pressure in the second accumulator 16 reaches to the first negative pressure set value Vs1, the third and fourth switching valves 18 and 19 are closed. After these steps the compressor 10 continues to increase the pressure in the first accumulator 13 and decrease the pressure in the second accumulator 16. If the pressure at the outlet terminal of the compressor 10 reaches to the second positive pressure set value Ps2 which is the set value of the positive pressure relief valve 23, the positive pressure relief valve 23 opens and keeps the positive pressure in the first accumulator 13 to the second positive pressure set value Ps2. If the pressure at inlet terminal of the compressor 10 reaches to the second negative pressure set value Vs2 which is the set value of the negative pressure relief valve 24, the negative pressure relief valve 24 opens and keeps the negative pressure in the second accumulator 16 to the second negative pressure set value Vs2. Therefore the pressures in the first and second accumulators 13 and 16 are prevented from being excessive pressures. At that time, because the compressor 10 has an outlet resistance applied by the second positive pressure set value Ps2 of the positive pressure relief valve 23 and an inlet resistance applied by the second negative pressure set value Vs2 of the negative pressure relief valve 24, the compressor 10 is prevented from an idle operation.

Under the negative pressure supplying mode, the negative pressure in the second accumulator 16 is regulated to the first negative pressure set value Vs1 at step S 10 and the positive pressure in the first accumulator 13 is regulated to the first positive pressure set value Ps1 at step S 12. If the sensed positive pressure Pm of the first pressure sensing means 21 reaches the first positive pressure set value Ps1, the third and fourth switching valves 18 and 19 are closed at step S 14. Thus, under the negative pressure supplying mode, after the pressures in the first and second accumulator 13 and 16 reach the set values, the compressor 10 has an outlet resistance applied by the second positive pressure set value Ps2 of the positive pressure relief valve 23 and an inlet resistance applied by the second negative pressure set value Vs2 of the negative pressure relief valve 24. The compressor 10 is prevented from an idle operation.

As mentioned above, when the pressure in the first accumulator 13 is regulated to the first positive pressure set value Ps1, the pressure in the first accumulator 13 is limited by the positive pressure relief valve 23 to the second positive pressure set value Ps2. When the presure in the second accumulator 16 is regulated to the first negative pressure set value Vs1, the pressure in the second accumulator 16 is limited by the negative pressure relief valve 24 to the second negative pressure set value Vs2. Thus the first positive and negative pressure set values are changed to the second positive and negative pressure set values.

In this embodiment, both the positive and negative pressures in the accumulators 13 and 16 are prevented from being excessive. However, if only the positive pressure might be prevented from being excessive, the positive pressure relief valve 23 will be provided. And if only the negative pressure might be prevented from being excessive, the negative pressure relief valve 24 will be provided. In case of providing only the positive pressure relief valve 24, when the pressure in the first accumulator 13 reaches to the first positive pressure set value Ps1 and the pressure in the second accumulator 16 reaches to the first negative pressure set value Vs1, the third switching valve 18 is closed and the fourth switching valve 19 is opened. In case of providing only the negative pressure relief valve, the third switching valve 18 is opened and the fourth switching valve 19 is closed.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. An apparatus for driving a medical appliance comprising:
   a positive pressure generating means having an outlet terminal;
   a first one-way valve means having an inlet terminal connected to said outlet terminal of said positive pressure generating means;
   a first accumulating means connected to an outlet terminal of said first one-way valve means;
   a first switching valve means connected to said first accumulating means;
   a first pressure sensing means for detecting a pressure between said first one-way valve means and said first switching valve means;
   a second switching valve means connected to an outlet terminal of said first switching valve means;

a second accumulating means connected to said second switching valve means;

a second one-way valve means having an inlet terminal connected to said second accumulating means and an outlet terminal connected to an inlet terminal of said positive pressure generating means;

a second pressure sensing means for detecting a pressure between said second switching valve means and said second one-way valve means;

a third switching valve means connected between said pressure generating means and said first one-way valve means for controlling communication of said pressure generating means with the atmosphere;

a fourth switching valve means connected between said pressure generating means and said second one-Way valve means for controlling communication of said pressure generating means with the atmosphere;

an isolator means having an inlet connected between said first and second switching valve means and an outlet adapted to be connected to a medical appliance for the alternate application of positive and negative pressures thereto; and an electronic control means connected to said valve means and said pressure sensing means for opening and closing said first and second switching valve means in accordance with predetermined timings to alternately apply positive and negative fluid pressures to said isolator means, for opening and closing said third and fourth switching valve means in accordance with both positive and negative pressure setting values provided in said electronic control means and output signals from said first and second pressure sensing means and for closing at least one of said third and fourth switching valve means when both of said output signals from said first and second pressure sensing means are above the setting values, respectively for regulating the pressures in said first and second accumulator means.

2. An apparatus for driving a medical appliance comprising:

a positive pressure generating means having an outlet terminal;

a first one-way valve means having an inlet terminal connected to said outlet terminal of said positive pressure generating means;

a first accumulating means connected to an outlet terminal of said first one-way valve means;

a first switching valve means connected to said first accumulating means;

a first pressure sensing means for detecting a pressure between said first one-way valve means and said first switching valve means;

a second switching valve means connected to an outlet terminal of said first switching valve means;

a second accumulating means connected to said second switching valve means;

a second one-way valve means having an inlet terminal connected to said second accumulating means and an outlet terminal connected to an inlet terminal of said positive pressure generating means;

a second pressure sensing means for detecting a pressure between said second switching valve means and said second one-way valve means;

a third switching valve means connected between said pressure generating means and said first one-way valve means for controlling communication of said pressure generating means with the atmosphere;

a fourth switching valve means connected between said pressure generating means and said second one-Way valve means for controlling communication of said pressure generating means with the atmosphere;

an isolator means having an inlet connected between said first and second switching valve means and an outlet adapted to be connected to a medical appliance for the alternate application of positive and negative pressures thereto; and an electronic control means connected to said valve means and said pressure sensing means for opening and closing said first and second switching valve means in accordance with predetermined timings to alternately apply positive and negative fluid pressures to said isolator means, for opening and closing said third and fourth switching valve means in accordance with both positive and negative pressure setting values provided in said electronic control means and output signals from said first and second pressure sensing means, for closing said fourth switching valve means when said first pressure sensing means detects a positive pressure above the positive pressure setting value and said second pressure sensing means detects a negative pressure below said negative pressure setting value and for closing said third switching valve means when said first pressure sensing means detects a positive pressure below the positive pressure setting value and second pressure sensing means detects a negative pressure above the negative pressure setting value.

3. An apparatus for driving a medical appliance comprising:

a positive pressure generating means having an outlet terminal;

a first one-way valve means having an inlet terminal connected to said outlet terminal of said positive pressure generating means;

a first accumulating means connected to an outlet terminal of said first one-way valve means;

a first switching valve means connected to said first accumulating means;

a first pressure sensing means for detecting a pressure between said first one-way valve means and said first switching valve means;

a second switching valve means connected to an outlet terminal of said first switching valve means;

a second accumulating means connected to said second switching valve means;

a second one-way valve means having an inlet terminal connected to said second accumulating means and an outlet terminal connected to an inlet terminal of said positive pressure generating means;

a second pressure sensing means for detecting a pressure between said second switching valve means and said second one-way valve means;

a third switching valve means connected between said pressure generating means and said first one-way valve means for controlling communication of said pressure generating means with the atmosphere;

a fourth switching valve means connected between said pressure generating means and said second one-Way valve means for controlling communication of said pressure generating means with the atmosphere;

an isolator means having an inlet connected between said first and second switching valve means and an outlet adapted to be connected to a medical appliance for the alternate application of positive and negative pressures thereto; and an electronic control means connected to said valve means and said pressure sensing means for opening and closing said first and second switching valve means in accordance with predetermined timings to alternately apply positive and negative fluid pressures to said isolator means, for opening and closing said third and fourth switching valve means in accordance with both positive and negative pressure setting values provided in said electronic control means and output signal means from said first and second pressure sensing means, and for closing said third and fourth switching valve means when said first and second pressure sensing means detect positive and negative pressures below said positive and negative pressure setting values, respectively.

* * * * *